US012484865B2

(12) United States Patent
Regensburger

(10) Patent No.: US 12,484,865 B2
(45) Date of Patent: Dec. 2, 2025

(54) SELECTIVE INTERNAL RADIATION THERAPY MAPPING VIA MICROBEADS WITH DIFFERENT CONTRAST MATERIALS

(71) Applicant: Varian Medical Systems, Inc., Palo Alto, CA (US)

(72) Inventor: Alois Regensburger, Poxdorf (DE)

(73) Assignee: Varian Medical Systems, Inc., Palo Alto, CA (US)

( * ) Notice: Subject to any disclaimer, the term of this patent is extended or adjusted under 35 U.S.C. 154(b) by 181 days.

(21) Appl. No.: 18/431,905

(22) Filed: Feb. 2, 2024

(65) Prior Publication Data

US 2025/0248671 A1 Aug. 7, 2025

(51) Int. Cl.

| | |
|---|---|
| ***A61B 6/00*** | (2024.01) |
| ***A61B 6/12*** | (2006.01) |
| ***A61B 6/42*** | (2024.01) |
| ***A61B 6/50*** | (2024.01) |
| ***A61K 49/04*** | (2006.01) |
| ***G16H 20/40*** | (2018.01) |

(52) U.S. Cl.

CPC .............. *A61B 6/12* (2013.01); *A61B 6/4241* (2013.01); *A61B 6/481* (2013.01); *A61B 6/504* (2013.01); *A61B 6/5235* (2013.01); *A61K 49/0419* (2013.01); *G16H 20/40* (2018.01)

(58) Field of Classification Search

None

See application file for complete search history.

(56) References Cited

U.S. PATENT DOCUMENTS

2018/0035960 A1* 2/2018 Haase ................ A61K 49/0419

* cited by examiner

*Primary Examiner* — Hoon K Song

(74) *Attorney, Agent, or Firm* — Duane Morris LLP

(57) ABSTRACT

A method includes determining a shunt fraction of microbeads by comparing a known ratio of a mixture of smaller microbeads loaded with a first contrast agent to larger microbeads loaded with a second contrast agent changes to a diffused ratio of the smaller microbeads to the larger microbeads after the mixture has been administered to a treatment site.

21 Claims, 3 Drawing Sheets

SELECTIVE INTERNAL RADIATION THERAPY MAPPING VIA MICROBEADS WITH DIFFERENT CONTRAST MATERIALS

TECHNICAL FIELD

This disclosure relates to selective internal radiation therapy (SIRT). More specifically, the disclosure relates to a method used to determine a vascular shunt fraction of arterial microbead injection using contrast mapping prior to SIRT treatment.

BACKGROUND

SIRT is a type of internal radiotherapy primarily used to treat cancer in the liver or cancer spreading from the liver. During SIRT, radioactive microbeads or microspheres are injected into blood vessels upstream of the treatment site or target tissue. It is intended that the microbeads get stuck in or clog small blood vessels in and around the cancer or tumor, and the radiation destroys the cancer cells. However, shunting or migration of the radioactive microbeads to tissue not being treated can have undesirable side effects.

For SIRT dosimetry with X-ray visible microbeads, it is desirable to determine a quantity of microbeads present in a target tissue volume and minimize a quantity of radioactive microbeads that shunt or migrate to non-targeted tissue. There is a clinically significant risk that some injected radioactive microbeads used during a SIRT injection will not stay inside or at the target tissue of interest (e.g., liver), but instead move to undesirable locations in a patient's body such as their lungs or stomach. Shunting blood vessels or other anatomical voids or irregular tumor tissue structures with a sufficient diameter for the radioactive microbeads to pass are necessary for this to happen.

To address this complication, conventionally a pre-treatment mapping session with biodegradable radioactive (MAA) microbeads is performed. After arterial injection of the radioactive MAA beads (e.g., Technetium 99 (Tc99)), imaging with positron emission tomography-computed tomography (PET-CT) or single-photon emission computed tomography (SPEC CT) shows the MAA microbeads shunting to the lung or stomach. This information can be used for treatment planning. However, such a mapping session separate from treatment requires coordinated scheduling of an angiography room and nuclear imaging resources. In addition to difficultly scheduling workflow, scheduling delivery of radioactive MAA microbeads has to be taken into account as these microbeads need to be preordered as they have a limited half life time of radioactive emission.

SUMMARY

The methods and apparatus described herein are directed to embodiments where X-Ray images of tissue including microbeads are used to estimate the microbead concentration and distribution in target tissue of interest and this estimation is used as input to a dosimetric calculation for the SIRT treatment of the target tissue. Microbeads can be made from MAA (macroaggregated albumin) which are biodegradable macroaggregate of human serum albumin. Biodegradable microbeads can also be made of other suitable materials including glass or a resin. This process can be used prior to or for treatment of a hypervascularized tumor such as hepatocellular carcinoma (HCC), which is the most common type of primary liver cancer.

According to an embodiment, to determine a SIRT shunt fraction from the liver, a test injection is performed of smaller mirobeads containing a first contrast material (e.g., Iodine) and larger beads containing a second contrast material (e.g., Barium, Tantalum, or Bismuth) in a known ratio. A spectrally resolved CT or cone-beam CT (CBCT) imaging system is used to determine the residual ratio of contrast-loaded smaller to larger beads in the target area sometime after injection. A shunt fraction for the smaller beads is calculated based on the observed change of ratio assuming that the larger microbeads are not shunted and the amount of larger microbeads remains in the treatments site.

Known spectral X-ray imaging approaches of material separation between multiple contrast agents for photon counting CT/CBCT or dual energy CT/CBCT are used in the disclosed method. The method provides easier logistics for the mapping treatment session as only a CBCT or an Angio-CT room is necessary, and no scheduling of SPECT/CT or PET/CT (nuclear) imaging is required. Additionally, time-critical preordering of radioactive MAA beads is not necessary. The described contrast-loaded microbeads should remain stable in a refrigerator for several months. The shunting determined using the disclosed method may not always be specific to the liver as the method could be used to map other organs or treatment areas.

To address the problems described above, in a disclosed embodiment, a method includes providing a mixture of smaller contrast-loaded microbeads and larger contrast-loaded microbeads in a known ratio or amount; waiting a first period of time after the mixture has been administered to a treatment site; and after the first period of time, determining a first shunt fraction of the mixture by correlating the known ratio to a diffused ratio of the smaller contrast-loaded microbeads to the larger contrast-loaded microbeads in the treatment site.

In an aspect, the mixture is biodegradable.

The method can further include waiting for the smaller contrast-loaded microbeads and the larger contrast-loaded microbeads to biodegrade.

In an aspect, the smaller contrast-loaded microbeads are loaded with a first contrast agent and the larger contrast-loaded microbeads are loaded with a second contrast agent.

The method can further include, after the first period of time, acquiring a spectrally resolvable image of the smaller contrast-loaded microbeads and the larger contrast-loaded microbeads in the treatment site.

In an aspect, the spectrally resolvable image is acquired by a 3D X-ray imaging system.

In an aspect, the diffused ratio is determined by calculating the smaller contrast-loaded microbeads and the larger contrast-loaded microbeads visible in a spectrally resolvable image of the treatment site.

The method can further include waiting a second period of time after the mixture has been administered to a treatment site; and after the second period of time, determining a second shunt fraction of the mixture.

In an aspect, in determining a shunt fraction of the mixture it is assumed that the larger contrast-loaded microbeads remain in the treatment site.

In an aspect, the smaller contrast-loaded microbeads are administered before the larger contrast-loaded microbeads.

In an aspect, a diameter of the larger contrast-loaded microbeads is at least 1.5 times a diameter of the smaller contrast-loaded microbeads.

The method can further include planning a SIRT treatment procedure taking into account the shunt fraction.

In another embodiment, a method includes determining a shunt fraction of microbeads by comparing a known ratio of a mixture of smaller microbeads loaded with a first contrast agent to larger microbeads loaded with a second contrast agent changes to a diffused ratio of the smaller microbeads to the larger microbeads after the mixture has been administered to a treatment site.

In an aspect, the diffused ratio is determined by acquiring a spectrally resolvable image of the treatment site, correlating a resolved density of the first contrast agent in the image to an amount of the smaller microbeads, and correlating a resolved density of the second contrast agent in the image to an amount of the larger microbeads.

The method can further include considering that the amount of larger microbeads administered to a treatment site does not change.

The method can further include waiting a period of time after the mixture has been administered to a treatment site before acquiring the spectrally resolvable image of the treatment site.

The method can further include planning a SIRT treatment procedure taking into account the shunt fraction.

The method can further include confirming degradation or existence of the mixture with a diagnostic X-ray image.

BRIEF DESCRIPTION OF THE DRAWINGS

The features and advantages of the present disclosures will be more fully disclosed in, or rendered apparent by the following detailed descriptions of example embodiments. The detailed descriptions of the example embodiments are to be considered together with the accompanying drawings wherein like numbers refer to like parts and further wherein.

DETAILED DESCRIPTION

Figure 1:
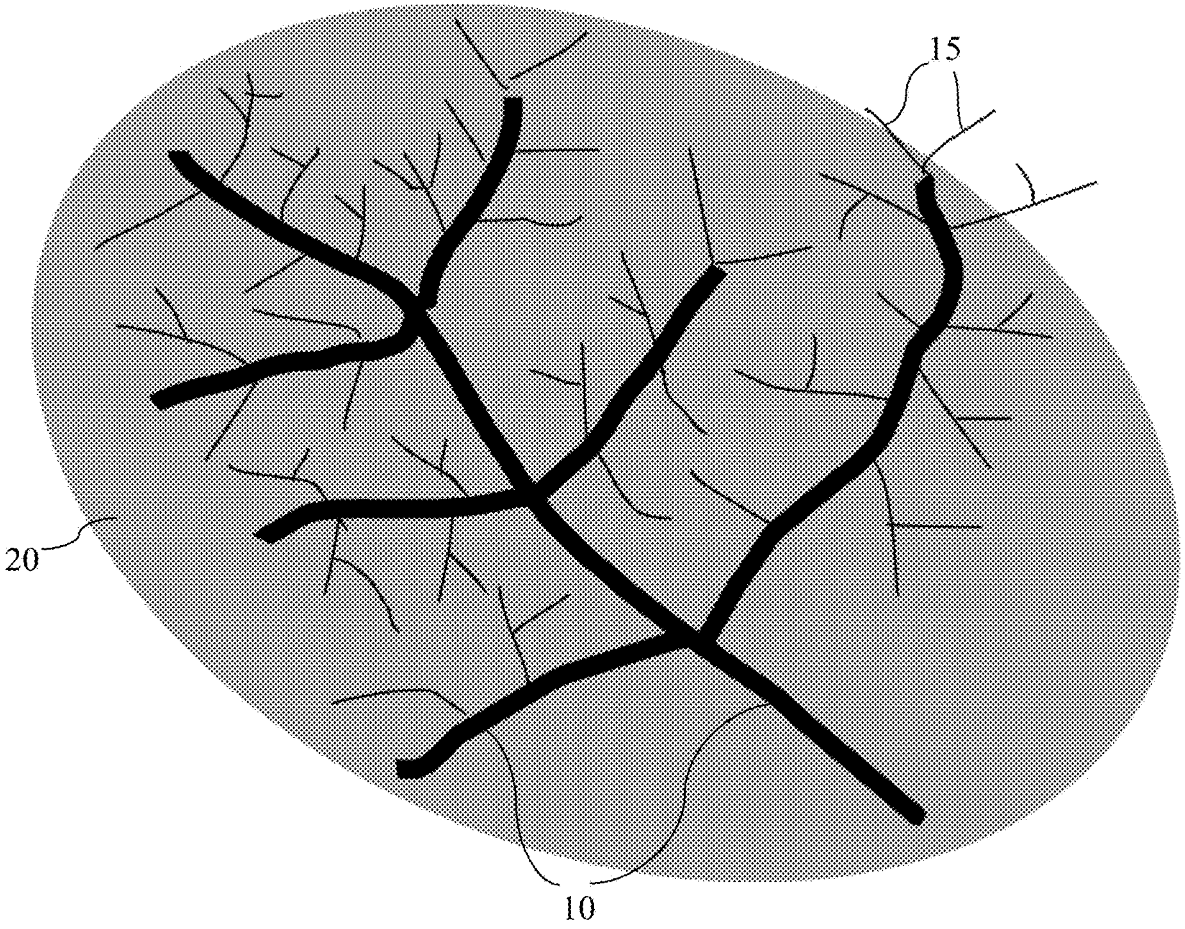
FIG. 1 represents blood vessels of an organ.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments.

The dark lines in FIG. 1 represent blood vessels of an organ surrounded by parenchyma or tumor tissue 20, represented as a gray oval. The medium to large blood vessels 10 and the microvasculature 15 are filled with a liquid contrast agent such as an iodine solution that has been injected upstream from the tissues. The parenchyma or tumor tissue 20 has a measurable contrast uptake via a body perfused blood volume (DynaPBV body) protocol. It is possible to image small blood vessels and tissue uptake of the liquid contrast agent. This is done by either directly resolving small individual blood vessels or by calculating a bulk/spatially averaged uptake of contrast agent in tissue and small blood vessels.

During SIRT, tiny glass or resin mircobeads including a radioactive isotope yttrium Y-90 (or possibly non-radioactive) are placed inside the blood vessels that feed a tumor or target tissue site. The injected microbeads, via the inclusion of highly X-ray visible materials in the microbeads, are directly visible in a 3D X-ray image. Typically, individual microbeads cannot be resolved in imaging, but all larger accumulations of microbeads, such as in arterial blood vessels of different sizes, are directly visible in the X-ray image. Smaller accumulations or freely distributed microbeads cannot be resolved without spectral methods such as dual energy or photon counting, and are only diffusely noticeable by a slight increase in the Hounsfield Unit (HU) value.

In some embodiments, a mixture of smaller microbeads and larger microbeads are administered to a target tissue, such as target tissue 20. The smaller microbeads contain a first X-ray visible contrast agent based on a first element, e.g. Iodine. The smaller microbeads can have a diameter in the range of 20-30 μm. The larger microbeads contain a second X-ray visible contrast agent based on a second element, e.g. Bismuth, Barium, Tantalum. The larger microbeads are large enough such that no or minimal shunting can occur where the larger microbeads have a diameter of 1.5 to 2 times the diameter of the smaller microbeads, i.e., 60-80 μm. For example, the larger microbeads can have a diameter of at least 1.5 times the diameter of the smaller microbeads. The second contrast agent element is different from the first contrast agent element such that their Z-number (atomic number) is far apart and/or they are very spectrally differentiable in their X-ray absorption characteristics. The smaller and the larger contrast-loaded microbeads are biodegradable, likely over several days. The ratio of smaller microbeads to larger microbeads can be 1:1 or adjusted to have a similar X-ray visibility of both types of microbeads, or adjusted to have an optimized spectral separability of the two contrast agents in spectral X-ray imaging. The imaging system can use dual energy or photon counting techniques, for example CT or CBCT.

Figure 2:
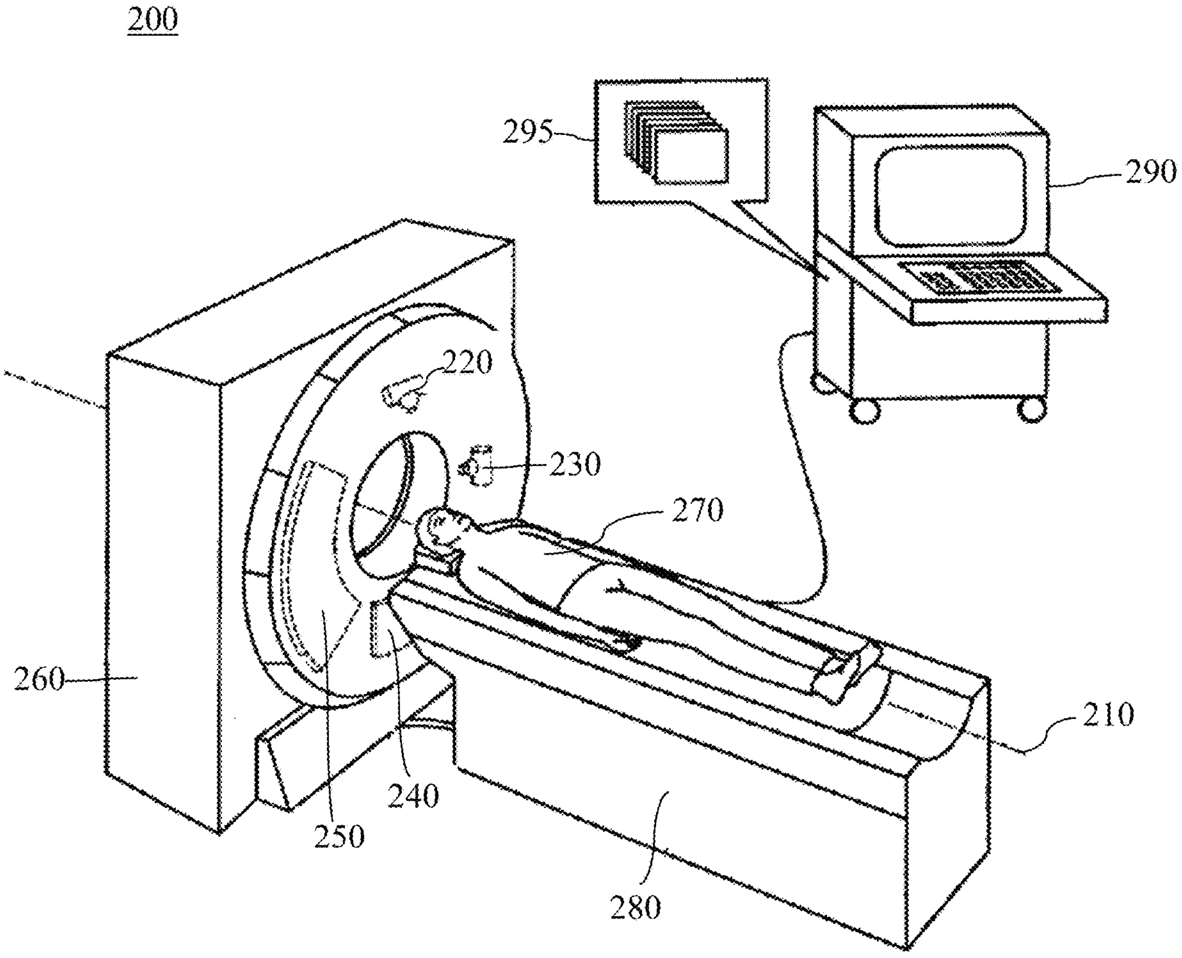
FIG. 2 is an example of an X-ray CT system that can be used to image microbeads and determine a shunt fraction according to an embodiment of the present disclosure.

FIG. 2 is an example of an X-ray CT system 200 that can be used to spectrally resolve a 3D X-ray image of the contrast-loaded microbeads. The X-ray CT system 200 can include X-ray sources 220 and 230, detectors 240 and 250, a gantry housing 260, a patient 270 on a patient bed 280, a system axis 210, a control and processing system 290, and a data storage 295. The control and processing system 290 can be a single computer or network of computers used to control the X-ray CT system 200, and interact with a clinician to perform image capture, image processing, data manipulation, calculations, and map generation in steps of the method described below with respect to FIG. 3. The X-ray CT system can be a photon counting CT system, or a dual energy dual source CT system.

Figure 3:
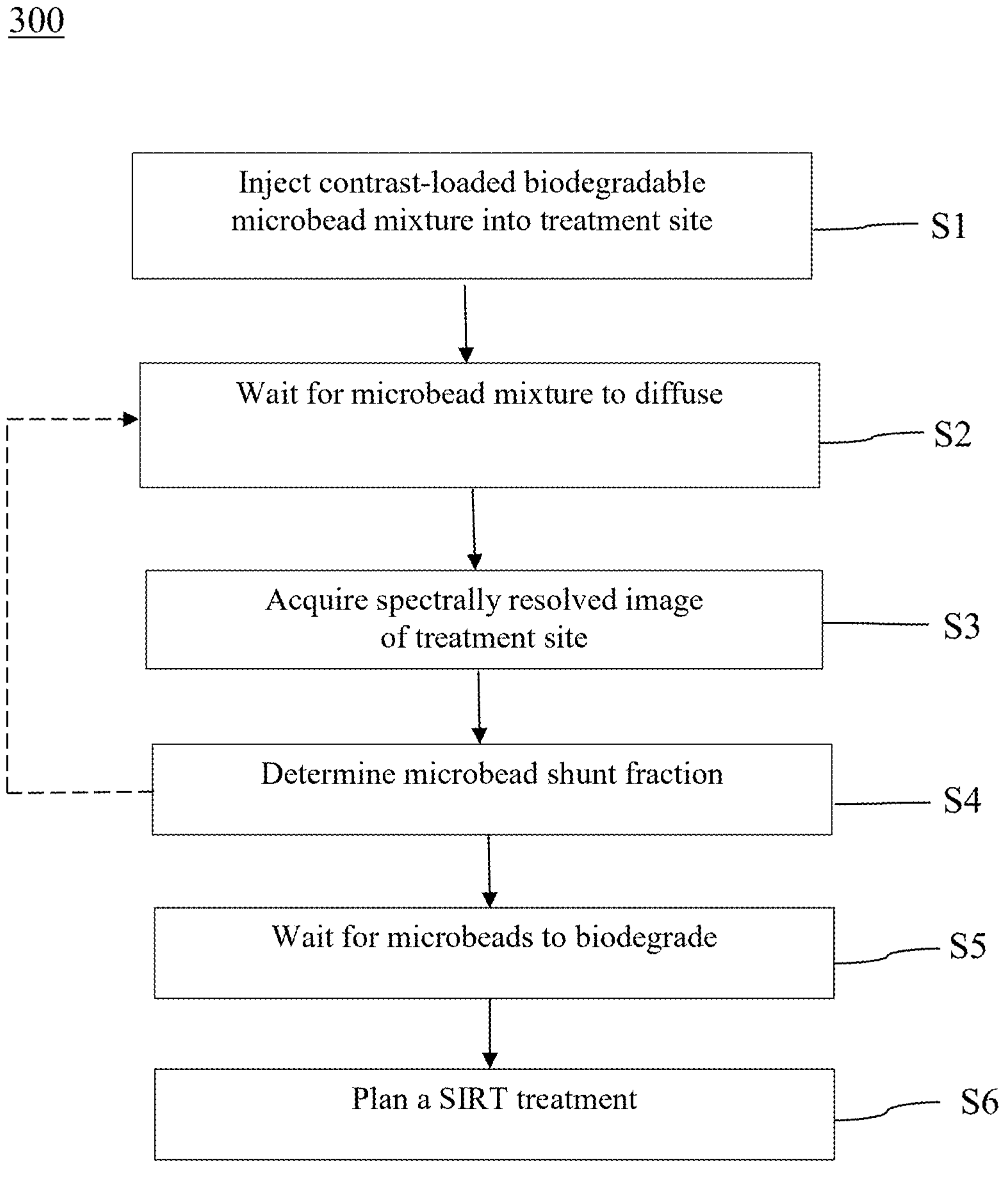
FIG. 3 is a flowchart including steps of a mapping method of imaging microbeads and determining a shunt fraction according to an embodiment of the present disclosure.

FIG. 3 is a flowchart including steps of a method 300 of mapping for SIRT treatment by imaging contrast-loaded microbeads and performing a shunt fraction calculation according to an embodiment of the present disclosure.

The disclosed mapping method 300 is meant to be performed prior to and as an input to providing SIRT to a patient. Any procedure injecting microbeads or material with different flow/infiltration dynamics than the liquid contrast agent could benefit from this method. For example, transarterial chemoembolization (TACE) with drug eluting beads, and injection of ultrasound contrast bubbles can benefit from this method.

Optionally, prior to performing the method 300, a clinician can perform vascular mapping of a treatment site via a contrasted scan of the arterial structure in the tissue of interest with a liquid contrast agent, for example a 3D X-ray angiogram in an angiography setting. This can be used to gather information to determine the injection location and estimate the amount of mircobeads to be administered, and to pre-exclude large shunting vessels through which the larger beads could pass through.

In step S1, a contrast-loaded biodegradable microbead mixture of smaller and larger microbeads in a known ratio can be administered at the selected injection location, i.e., the treatment site. For example, the treatment site can be the entire liver; a tumor in the liver, and optionally including a margin; a portion of the liver or liver segment; the tissue of the liver arterially supplied "downstream" from the vascular injection position (also known as "tissue at risk" or "vascular supply territory of injection location"); or another area of target tissue. The smaller microbeads can have a diameter in a range of about 10 to 30 μm and be loaded with a first contrast agent. The larger microbeads can have a diameter of at least 1.5 to 2 times that of the smaller microbeads, i.e., 60 to 80 μm and be loaded with a second contrast agent different than that loaded with the smaller microbeads. Experience of the clinical staff and information obtained from a vascular mapping with a liquid contrast agent can be used to select a sufficient amount of microbeads to inject to fill the vessels of interest with the assumption that the larger microbeads are not shunted.

Optionally, the amount of contrast-loaded microbeads injected can be measured, via 2D X-ray absorption and a known injection speed, or via volumetric measurement in the injection syringe/apparatus. This could allow for additional calibration or confidence test during the later evaluation (e.g., to determine whether all larger beads are still in the target tissue area). Optionally, it should also be understood that only smaller microbeads can be injected first, followed by a carefully matched amount of larger microbeads in a second injection, fulfilling the desired ratio of smaller to larger contrast-loaded microbeads.

In step S2, the injected contrast-loaded microbeads are allowed to diffuse for a period of time. For example, the wait time can be 5-20 minutes and verified by previous clinical study. It is expected that the smaller microbeads will migrate or diffuse from the area of the injection, i.e., the treatment site, and that the larger microbeads will stay in the treatment site.

In step S3, a spectrally resolved 3D X-ray image is acquired of the treatment site by the imaging system (e.g., CBCT, CT, or other). It is expected that the treatment site is defined or segmented in this dataset. Alternatively, the dataset can be fused/registered where a previously obtained image of the treatment site is overlaid with the acquired spectrally resolved 3D X-ray image.

Here, the spectrally resolved 3D X-ray image is taken of the treatment site where signal to noise is maximized. It is expected that the larger microbeads are not shunted and at least a portion of the smaller microbeads will be shunted and diffused/lost to locations in anatomy outside of the treatment site.

In step S4, a shunt fraction of the microbeads is calculated. The spectrally resolved 3D X-ray image allows a determination of a spatially resolved ratio between the two different contrast agent materials, which are in the smaller and the larger microbeads, respectively. The known contrast agent loading per smaller/larger microbeads is used to determine the number and/or ratio of smaller to larger microbeads. That is, the signal, spatial distribution, concentration, amount, or density maps for the different contrast agents correlate to the size of microbeads to which they are loaded. A density of the different microbead sizes and ratio of the smaller to larger microbeads can be calculated. Integrating/averaging a local microbead size ratio over the area of the treatment site will provide an average ratio of smaller to larger microbeads within the treatment site. The shunt fraction can be determined by comparing the average microbead ratio determined via the imaging to the ratio of administered microbeads. This assumes that the amount of larger microbeads stays constant as the larger microbeads remain in the treatment site while some of the smaller microbeads have likely shunted towards other anatomy. Such shunting becomes apparent by a change of the ratio of the smaller to larger microbeads after administration.

It is understood that in actuality, there might be large "ways out" of the treatment area like unintended backflow through larger vessels during injection. But it is assumed that in this case, these large "ways out" would carry away the initially injected ratio of smaller and larger microbeads. This situation does not impede the method, as the measurement is a relative one-additional changes that take away the initially injected ratio of smaller and larger microbeads will not alter the shunt measurement relying on relative values.

In some embodiments, steps S2 to S4 can be repeated as desired to gain shunting information, as indicated by the dashed arrow in FIG. 3. For example, the shunt fraction can be determined after waiting different lengths of time, thereby calculating one or more "earlier shunt fractions" and one or more "later shunt fractions". Repeating steps S2 to S4 can provide an insight into the mechanism of shunting. Earlier shunting indicates vessel shunts, whereas later shunting indicates migration of small microbeads via degenerate tumor tissue. Later shunts can be desirable to some degree, as they would indicate the local presence of small microbeads in tumor tissue. Preferably, the later shunt fraction is measured after a waiting period that is longer than two thirds of the half life time of the radioactive beads injected in a future treatment session, whereas the earlier shunt fraction is measured after a waiting period that is shorter than one third of the half life time.

Other information can also be obtained from the spectral X-ray imaging. For example, localized variations in the ratio of smaller to larger microbeads can be used to determine a fraction between small and large vasculature. This can indicate degeneration of the arterial supply system by a tumor, and be used to refine tumor segmentation. Also, localized hot spots in the concentration of the smaller beads can be used as a predictor for hot spots in the dosimetry of the later SIRT treatment.

In step S5, the biodegradable microbeads are allowed to degrade over a period of time. The degradation time is a function of the microbeads used in the mapping method 300 and expected to be specified by the manufacturer. Optionally but not necessary, the degradation and/or existence of the contrast-loaded microbeads can be confirmed with a 2D or 3D diagnostic X-ray image. It is necessary to ensure that the larger microbeads have degraded and not blocking vessels before the SIRT treatment.

In step S6, a SIRT treatment can be planned considering the shunt fraction determined. The SIRT treatment can be performed after the microbeads used in the mapping method 300 have sufficiently biodegraded. The SIRT treatment can be planned and/or performed with similar administration parameters used and/or information gained from the mapping method 300. Radioactive microbeads for SIRT in a treatment injection can be of a similar size or size distribution taking into consideration the expected shunt fraction for smaller microbeads determined in the mapping method 300.

Additionally, or alternatively, a portion of the above-described method can be implemented as a non-transitory computer-readable storage medium embodied thereon a program executable by a processor for performing a method of various embodiments.

Also, the various methods or processes outlined herein can be coded as software that is executable on one or more processors that employ any one of a variety of operating systems or platforms. Additionally, such software can be written using any of a number of suitable programming languages and/or programming or scripting tools, and also can be compiled as executable machine language code or intermediate code that is executed on a framework or virtual machine. Typically, the functionality of the program modules can be combined or distributed as desired in various embodiments.

Also, the embodiments of the disclosure can be embodied as a method, of which an example has been provided. The steps or acts performed as part of the method can be ordered in any suitable way. Accordingly, embodiments can be constructed in which steps are performed in an order different than illustrated, which can include performing some steps concurrently, even though shown as sequential steps in illustrative embodiments.

The foregoing is provided for purposes of illustrating, explaining, and describing embodiments of these disclosures. Modifications and adaptations to these embodiments will be apparent to those skilled in the art and may be made without departing from the scope or spirit of these disclosures.

The following is a list of non-limiting illustrative embodiments disclosed herein:

- Illustrative embodiment 1. A method comprising: providing a mixture of smaller contrast-loaded microbeads and larger contrast-loaded microbeads in a known ratio; waiting a period of time after the mixture has been administered to a treatment site; and after the period of time, determining a shunt fraction of the mixture by correlating the known ratio to a diffused ratio of the smaller contrast-loaded microbeads to the larger contrast-loaded microbeads in the treatment site.
- Illustrative embodiment 2. The method of illustrative embodiment 1, wherein the mixture is biodegradable.
- Illustrative embodiment 3. The method of any of illustrative embodiments 1 and 2, further comprising waiting for the smaller contrast-loaded microbeads and the larger contrast-loaded microbeads to biodegrade.
- Illustrative embodiment 4. The method of any of illustrative embodiments 1-3, wherein the smaller contrast-loaded microbeads are loaded with a first contrast agent and the larger contrast-loaded microbeads are loaded with a second contrast agent.
- Illustrative embodiment 5. The method of any of illustrative embodiments 1-4, further comprising, after the period of time, acquiring a spectrally resolvable image of the smaller contrast-loaded microbeads and the larger contrast-loaded microbeads in the treatment site.
- Illustrative embodiment 6. The method of any of illustrative embodiments 1-5, wherein the spectrally resolvable image is acquired by a 3D X-ray imaging system.

- Illustrative embodiment 7. The method of any of illustrative embodiments 1-6, wherein the diffused ratio is determined by calculating the smaller contrast-loaded microbeads and the larger contrast-loaded microbeads visible in a spectrally resolvable image of the treatment site.
- Illustrative embodiment 8. The method of any of illustrative embodiments 1-7, further comprising: waiting a second period of time after the mixture has been administered to a treatment site; and after the second period of time, determining a second shunt fraction of the mixture.
- Illustrative embodiment 9. The method of any of illustrative embodiments 1-8, wherein in determining a shunt fraction of the mixture it is assumed that the larger contrast-loaded microbeads remain in the treatment site.
- Illustrative embodiment 10. The method of any of illustrative embodiments 19, wherein the smaller contrast-loaded microbeads are administered before the larger contrast-loaded microbeads.
- Illustrative embodiment 11. The method of any of illustrative embodiments 1-10, wherein a diameter of the larger contrast-loaded microbeads is at least 1.5 times a diameter of the smaller contrast-loaded microbeads.
- Illustrative embodiment 12. The method of any of illustrative embodiments 1-11, further comprising planning a SIRT treatment procedure taking into account the shunt fraction.
- Illustrative embodiment 13. A method comprising determining a shunt fraction of microbeads by comparing a known ratio of a mixture of smaller microbeads loaded with a first contrast agent to larger microbeads loaded with a second contrast agent changes to a diffused ratio of the smaller microbeads to the larger microbeads after the mixture has been administered to a treatment site.
- Illustrative embodiment 14. The method of illustrative embodiment 13, wherein the mixture is biodegradable.
- Illustrative embodiment 15. The method of illustrative embodiments 13-14, wherein the smaller contrast-loaded microbeads are loaded with a first contrast agent and the larger contrast-loaded microbeads are loaded with a second contrast agent.
- Illustrative embodiment 16. The method of any of illustrative embodiments 12-15, wherein the diffused ratio is determined by acquiring a spectrally resolvable image of the treatment site, correlating a resolved density of the first contrast agent in the image to an amount of the smaller microbeads, and correlating a resolved density of the second contrast agent in the image to an amount of the larger microbeads.
- Illustrative embodiment 17. The method of any of illustrative embodiments 12-16, further comprising considering that the amount of larger microbeads administered to a treatment site does not change.
- Illustrative embodiment 18. The method of any of illustrative embodiments 12-17, further comprising waiting a period of time after the mixture has been administered to a treatment site before acquiring the spectrally resolvable image of the treatment site.
- Illustrative embodiment 19. The method of any of illustrative embodiments 12-18, further comprising planning a SIRT treatment procedure taking into account the shunt fraction.

Illustrative embodiment 20. The method of any of illustrative embodiments 12-19, wherein a diameter of the larger microbeads is at least 1.5 times a diameter of the smaller microbeads.

Illustrative embodiment 21. The method of any of illustrative embodiments 12-20, further comprising confirming existence of the mixture with a diagnostic X-ray image.

What is claimed is:

1. A method comprising:

providing a mixture of smaller contrast-loaded microbeads and larger contrast-loaded microbeads in a known ratio;

waiting a first period of time after the mixture has been administered to a treatment site; and after the first period of time, determining a first shunt fraction of the mixture by correlating the known ratio to a diffused ratio of the smaller contrast-loaded microbeads to the larger contrast-loaded microbeads in the treatment site.

2. The method of claim 1, wherein the mixture is biodegradable.

3. The method of claim 2, further comprising waiting for the smaller contrast-loaded microbeads and the larger contrast-loaded microbeads to biodegrade.

4. The method of claim 1, wherein the smaller contrast-loaded microbeads are loaded with a first contrast agent and the larger contrast-loaded microbeads are loaded with a second contrast agent.

5. The method of claim 1, further comprising, after the first period of time, acquiring a spectrally resolvable image of the smaller contrast-loaded microbeads and the larger contrast-loaded microbeads in the treatment site.

6. The method of claim 5, wherein the spectrally resolvable image is acquired by a 3D X-ray imaging system.

7. The method of claim 1, wherein the diffused ratio is determined by calculating the smaller contrast-loaded microbeads and the larger contrast-loaded microbeads visible in a spectrally resolvable image of the treatment site.

8. The method of claim 1, further comprising:

waiting a second period of time after the mixture has been administered to a treatment site; and after the second period of time, determining a second shunt fraction of the mixture.

9. The method of claim 1, wherein in determining a shunt fraction of the mixture it is assumed that the larger contrast-loaded microbeads remain in the treatment site.

10. The method of claim 1, wherein the smaller contrast-loaded microbeads are administered before the larger contrast-loaded microbeads.

11. The method of claim 1, wherein a diameter of the larger contrast-loaded microbeads is at least 1.5 times a diameter of the smaller contrast-loaded microbeads.

12. The method of claim 1, further comprising planning a SIRT treatment procedure taking into account the shunt fraction.

13. A method comprising determining a shunt fraction of microbeads by comparing a known ratio of a mixture of smaller microbeads loaded with a first contrast agent to larger microbeads loaded with a second contrast agent changes to a diffused ratio of the smaller microbeads to the larger microbeads after the mixture has been administered to a treatment site.

14. The method of claim 13, wherein the mixture is biodegradable.

15. The method of claim 13, wherein the smaller contrast-loaded microbeads are loaded with a first contrast agent and the larger contrast-loaded microbeads are loaded with a second contrast agent.

16. The method of claim 13, wherein the diffused ratio is determined by acquiring a spectrally resolvable image of the treatment site, correlating a resolved density of the first contrast agent in the image to an amount of the smaller microbeads, and correlating a resolved density of the second contrast agent in the image to an amount of the larger microbeads.

17. The method of claim 16, further comprising considering that the amount of larger microbeads administered to a treatment site does not change.

18. The method of claim 13, further comprising waiting a period of time after the mixture has been administered to a treatment site before acquiring the spectrally resolvable image of the treatment site.

19. The method of claim 13, further comprising planning a SIRT treatment procedure taking into account the shunt fraction.

20. The method of claim 13, wherein a diameter of the larger microbeads is at least 1.5 times a diameter of the smaller microbeads.

21. The method of claim 13, further comprising confirming existence of the mixture with a diagnostic X-ray image.

* * * * *